US012773108B2

(12) United States Patent
Cheng et al.

(10) Patent No.: US 12,773,108 B2
(45) Date of Patent: Oct. 27, 2026

(54) AUGMENTED REALITY URETEROSCOPE SYSTEM

(71) Applicant: C. R. Bard, Inc., Franklin Lakes, NJ (US)

(72) Inventors: Jason Jishen Cheng, Avondale Estates, GA (US); Brendan Tan-Fahed, Potomac, MD (US); John D. Sangiorgio, Athens, GA (US); Wanfei Yang, Decatur, GA (US); Paul R. Hess, Snellville, GA (US)

(73) Assignee: C. R. Bard, Inc., Franklin Lakes, NJ (US)

(*) Notice: Subject to any disclaimer, the term of this patent is extended or adjusted under 35 U.S.C. 154(b) by 198 days.

(21) Appl. No.: 18/566,961

(22) PCT Filed: Jun. 3, 2022

(86) PCT No.: PCT/US2022/032131
§ 371 (c)(1),
(2) Date: Dec. 4, 2023

(87) PCT Pub. No.: WO2022/256632
PCT Pub. Date: Dec. 8, 2022

(65) Prior Publication Data

US 2024/0268655 A1 Aug. 15, 2024

Related U.S. Application Data

(60) Provisional application No. 63/197,142, filed on Jun. 4, 2021.

(51) Int. Cl.
*A61B 1/307* (2006.01)
*A61B 1/00* (2006.01)
(Continued)

(52) U.S. Cl.
CPC ........ *A61B 1/307* (2013.01); *A61B 1/000094* (2022.02); *A61B 1/000096* (2022.02);
(Continued)

(58) Field of Classification Search
CPC .............. A61B 1/307; A61B 1/000094; A61B 1/000096; A61B 1/0005; A61B 1/005;
(Continued)

(56) References Cited

U.S. PATENT DOCUMENTS 8,535,250 B2 * 9/2013 Owen ...................... A61N 7/02 600/407
9,254,075 B2 * 2/2016 Wolf ................ A61B 17/22012
(Continued)

FOREIGN PATENT DOCUMENTS

WO 2022256632 A1 12/2022

OTHER PUBLICATIONS

PCT/US2022/032131 filed Jun. 3, 2022 International Search Report and Written Opinion dated Sep. 13, 2022.

*Primary Examiner* — Anh Tuan T Nguyen
*Assistant Examiner* — Shankar Raj Ghimire
(74) *Attorney, Agent, or Firm* — Rutan & Tucker LLP

(57) ABSTRACT

A ureteroscope system including a ureteroscope configured for insertion into a urinary tract of a patient body is disclosed herein. The system can include an image processing module having a console with one or more processors and memory having logic stored thereon. The logic can perform various operations including providing a ureteroscope video image where transient objects have been removed to provide unobstructed visibility of persistent objects. The logic can perform other operations including object tracking, object highlighting, and object sizing. Overlays can provide for the
(Continued)

depiction of indicia on top of ureteroscope images A method of performing a lithotripsy procedure in conjunction with the system is also disclosed.

14 Claims, 9 Drawing Sheets

(51) Int. Cl.

| | |
|---|---|
| ***A61B 90/00*** | (2016.01) |
| *A61B 1/005* | (2006.01) |
| *A61B 1/05* | (2006.01) |

(52) U.S. Cl.
CPC ............ *A61B 1/0005* (2013.01); *A61B 1/005* (2013.01); *A61B 1/05* (2013.01); *A61B 2090/365* (2016.02)

(58) Field of Classification Search
CPC ................ A61B 1/05; A61B 2090/365; A61B 1/000095
See application file for complete search history.

(56) References Cited

U.S. PATENT DOCUMENTS

| | | | | |
|---|---|---|---|---|
| 2007/0203475 | A1* | 8/2007 | Fischer | A61B 17/221 604/530 |
| 2013/0002844 | A1* | 1/2013 | Shida | A61B 1/000094 348/E7.085 |
| 2015/0313444 | A1* | 11/2015 | Wolf | A61B 17/22004 600/103 |
| 2018/0220938 | A1* | 8/2018 | Watschke | A61B 5/1107 |
| 2021/0082092 | A1* | 3/2021 | Sargent | G06T 5/50 |
| 2021/0150706 | A1* | 5/2021 | Chen | G06T 7/13 |
| 2021/0196398 | A1* | 7/2021 | Ye | A61B 1/042 |
| 2022/0354352 | A1* | 11/2022 | Ozao | A61B 1/045 |
| 2023/0130679 | A1* | 4/2023 | Avolos | A61B 18/1492 600/300 |
| 2023/0190078 | A1* | 6/2023 | Clayman | A61B 1/0684 600/562 |
| 2024/0268655 | A1* | 8/2024 | Cheng | A61B 1/307 |

* cited by examiner

AUGMENTED REALITY URETEROSCOPE SYSTEM

PRIORITY

This application is a U.S. national stage application of International Application No. PCT/US2022/032131, filed Jun. 3, 2022, which claims the benefit of priority to U.S. Provisional Application No. 63/197,142, filed Jun. 4, 2021, each of which is incorporated by reference in its entirety into this application.

BACKGROUND

Kidney stones may be treated in various ways. Small kidney stones may pass through the urinary tract without treatment. Larger kidney stones or kidney stones that block the urinary tract may need to be removed via a medical procedure. Laser lithotripsy is a procedure for removing a calculus (e.g., a kidney stone) from the urinary tract of the patient. Laser lithotripsy includes inserting a laser optical fiber through the urinary tract to the calculus. The laser is then activated to break the calculus into small pieces that can be passed naturally by the patient or removed by a retrieval instrument. A typical procedure includes inserting a ureteroscope through the urethra, bladder, ureter and if necessary, into the kidney so that a distal tip of the scope is positioned adjacent the calculus. The laser optical fiber is inserted through a working channel of the ureteroscope to the calculus. The laser is then activated to break up the calculus into fragments small enough to be retrieved via a retrieval device such as a basket device or to be passed naturally by the patient through the urinary tract.

During laser ablation of the kidney stone, small fragments (e.g., fast moving dust particles) may be separated from the stone and suspended in urinary fluid. The small fragments may be so numerous so as to affect the visibility of objects through the urinary fluid. In some instances, the small fragments may significantly obstruct the view of larger fragments causing difficulty in further performance of the lithotripsy process. Such difficulty may inhibit identification and tracking of larger stone fragments that require further ablation. In some instances, an operator may need to pause the ablation process to reacquire visibility and retarget larger stone fragments.

Accordingly, disclosed herein are ureteroscope systems and methods that enhance the visibility of objects such as kidney stone fragments via a ureteroscope, tracking the fragments, and assessing a size of fragments during a laser lithotripsy procedure.

SUMMARY OF THE INVENTION

Briefly summarized, disclosed herein is a ureteroscope system including a ureteroscope configured for insertion into a urinary tract of a patient body. The ureteroscope includes an elongate flexible shaft having a camera disposed at a distal end thereof and an image processing module operatively coupled with the ureteroscope. The module includes a console having one or more processors and a non-transitory computer-readable medium. Logic stored on the medium, when executed by the one or more processors, is configured to perform various operations as summarized below.

The operations include receiving imaging data and defining a first image and a second image from the imaging data. The first image includes a plurality of objects including a first subset of the plurality of objects that obstructs the visibility of one or more objects of a second subset of the plurality of objects in the first image. In the second image, the one or more obstructed objects in the first image are visibly unobstructed. The operations include rendering the first image or the second image on a display of the system.

The imaging data may include video imaging data, and the first and second images may include video images. The objects may include fragments of a kidney stone.

The operations may further include removing the first subset of the plurality of objects from the first image to define the second image. In some embodiments, the second subset includes objects that are persistent within the first image, and the first subset includes objects that are transient within the first image.

The operations may further include: (i) tracking the locations of one or more objects within the first image or the second image; and (ii) defining a tracking image overlay, where the tracking overlay includes tracking indicia associated with the tracked objects. The operations may further include rendering the tracking overlay on top of the first image or the second image on the display.

The operations may further include: (i) identifying circumferential edges of one or more objects within the first image or the second image; (ii) highlighting the circumferential edges in an image overlay; and (iii) rendering the edge-highlighting overlay on top of the first image or the second image on the display.

The operations may further include: (i) defining sizes of one or more objects within the first image or the second image by calculating an area enclosed by the circumferential edge; and (ii) defining a sizing image overlay that includes size indicia associated with the sized objects, where each size indicium provides a visual indication of the respective object's size. The operations may further include rendering the sizing overlay on top of the first image or the second image on the display.

The operations may further include comparing each calculated area with an area limit stored in the non-transitory computer-readable medium and modifying the size indicium if the respective calculated area exceeds the area limit.

The operations may further include defining maximum lengths of one or more objects within the first image or the second image, where each maximum length is defined by a maximum distance between two points of the circumferential edge of the respective object. The operations may further include defining a length image overlay, where the length overlay includes a line indicium visually representing each respective maximum length, and the operations may further include rendering the length overlay on top of the first image or the second image on the display.

Also summarized herein is a method of performing a lithotripsy procedure on a patient. The method includes inserting a ureteroscope within a urinary tract of the patient; receiving imaging data from the ureteroscope; defining a first image of kidney stone fragments from the imaging data; and rendering a second image on a display, where the second image includes one or more persistent fragments of the first image, and omits one or more transient fragments of the first image. The method further includes ablating a fragment of the second image and removing an ablated portion of the fragment from the second image.

The method may further include defining a circumferential edge of the fragment and overlaying the second image with an edge indicium associated with the fragment, where the edge indicium visually highlights the circumferential edge of the fragment in the second image.

The method may further include overlaying the second image with a size indicium associated with the fragment, where the size indicium visually indicates a size of the fragment in the second image.

The method may further include overlaying the second image with a location indicium associated with the fragment, where the location indicium tracts displacement of the fragment in the second image.

The method may further include overlaying the second image with a length indicium associated with the fragment, where the length indicium depicts a maximum length of the fragment in the second image.

The method may further include the step of rendering a third image on the display, where the third image is a high-contrast black-and-white view of the second image.

The method may further include providing an image processing module operatively coupled with the ureteroscope that includes a console having one or more processors and a non-transitory computer-readable medium. Logic stored on the medium is configured such that, when executed by the one or more processors, performs operations including one or more of the steps summarized above.

These and other features of the concepts provided herein will become more apparent to those of skill in the art in view of the accompanying drawings and following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Figure 1A:
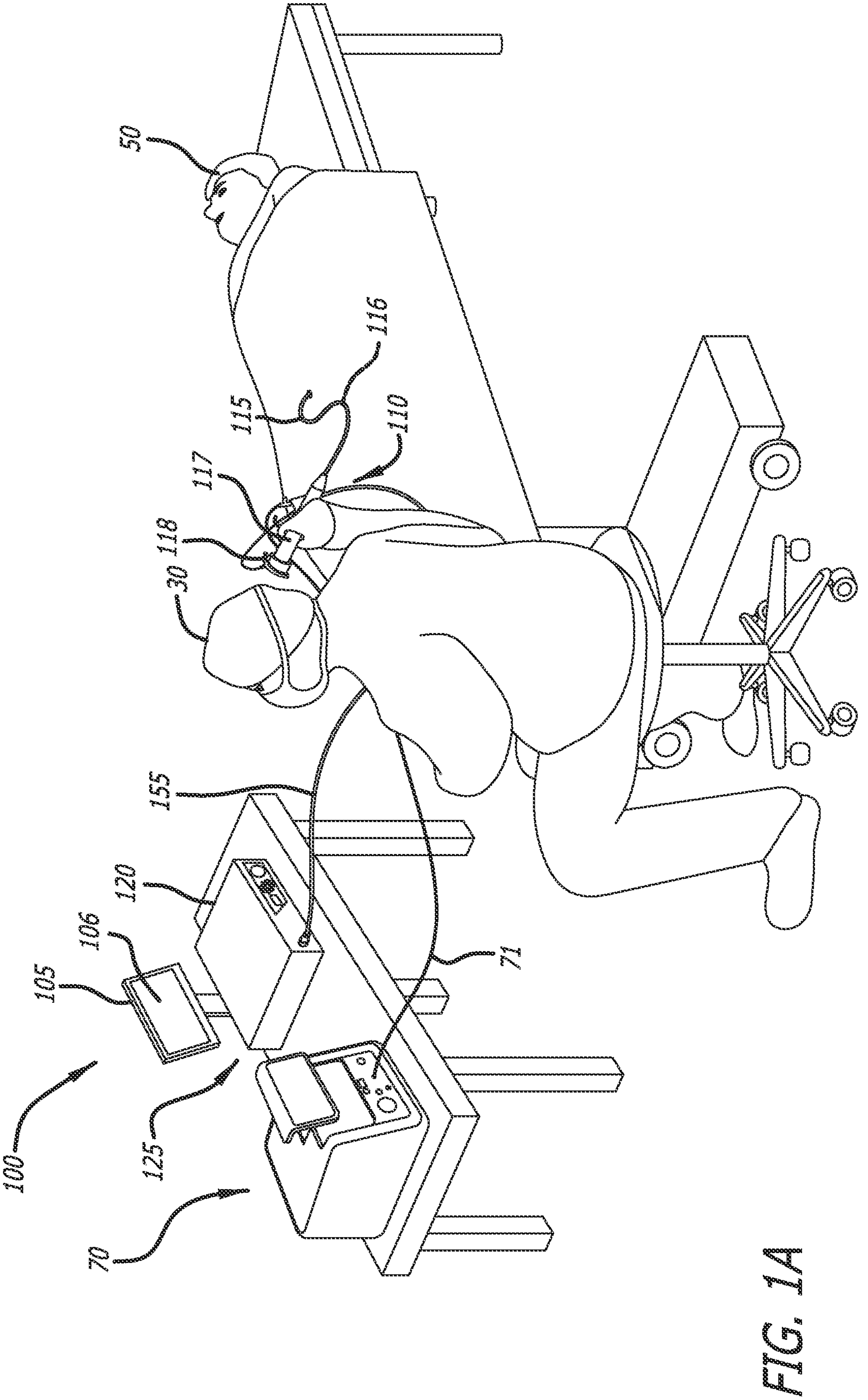
FIG. 1A illustrates a ureteroscope system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," "upward," "downward," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. Also, the words "including," "has," and "having," as used herein, including the claims, shall have the same meaning as the word "comprising."

Lastly, in the following description, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps, or acts are in some way inherently mutually exclusive.

Unless defined otherwise, all technical and scientific terms used herein have the same meaning as commonly understood by those of ordinary skill in the art.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

In certain situations, the term "logic" is representative of hardware, firmware, and/or software that is configured to perform one or more functions. As hardware, the logic may include circuitry having data processing or storage functionality. Examples of such circuitry may include, but are not limited or restricted to a microprocessor, one or more processor cores, a programmable gate array, a microcontroller, an application specific integrated circuit, wireless receiver, transmitter and/or transceiver circuitry, semiconductor memory, or combinatorial logic.

FIG. 1A illustrates an embodiment of a ureteroscope system 100 shown within a medical treatment environment. An operator 30 (e.g., a doctor) is shown performing an invasive treatment on a patient 50. The ureteroscope system 100 includes the ureteroscope 110 coupled with an imaging module 120. The ureteroscope 110 includes an elongate flexible shaft 115 configured for insertion within a urinary tract of the patient 50. The shaft 170 includes a camera (not shown) at a distal end of the shaft 170 and a working channel 116 extending along the shaft 170. During operation, images acquired by the camera are rendered on a display 105 coupled with the imaging module 120. The display 105 may also include a graphical user interface (GUI) 106. The operator 30 is shown using a urological laser instrument 70 configured for performing a laser lithotripsy procedure. The laser instrument 70 includes a fiber optic laser 71 inserted into the working channel 116.

During the treatment, the flexible shaft 115 of the ureteroscope 110 is inserted into the urinary tract of the patient 50 to a treatment location. The imaging module 120 renders images on the display 105 as acquired via the camera at the distal end of the shaft 115. The images show tissue and other objects (e.g., a kidney stone) at the treatment location. The operator 30 performs the treatment via operation of the laser instrument 70 while viewing the images acquired by the ureteroscope 110 and rendered on the display 105.

In some embodiments, the ureteroscope 110 may include a remote interface 118. The remote interface 118 is communicatively coupled with the imaging module 120 and may facilitate operation of the imaging system 100 via the handle 117.

A treatment procedure may typically include positioning the working distal end of the laser shaft 71 at a desired location as verified by the acquired images. The operator 30, via manipulation of the handle 117 of the ureteroscope 110, may position the distal end of the ureteroscope 110 at the desired location and aim the distal end of the fiber optic laser 71 at objects to be ablated such as a kidney stone or fragments thereof. During ablation of the kidney stone, the operator 30 may reposition the ureteroscope 110 several times to view different fragments of the kidney stone and re-aim the fiber optic laser 71 at the different fragments.

During ablation of the kidney stone, fragments of different sizes are broken off and separated from stone. Some fragments may be small enough to exit the patient via the urinary tract without further fragmentation. Other fragments may require further ablation or removal from the patient via a retrieval device. As such visibility of the fragments helps facilitate further ablation or retrieval. In some instances, the quantity of separated fragments may so numerous so as to obstruct visibility of other objects via the ureteroscope 110.

Figure 1B:
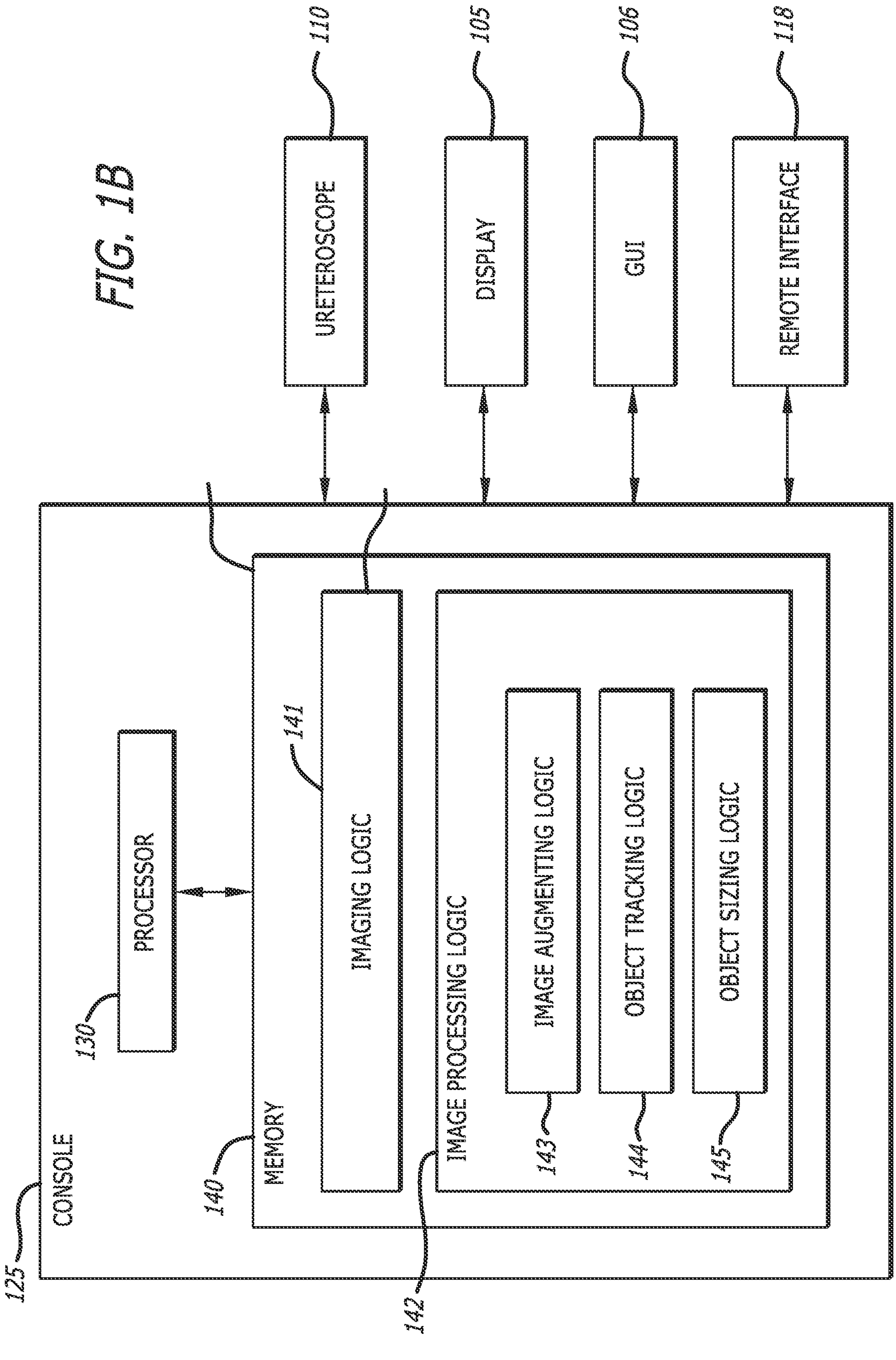
FIG. 1B illustrates a block diagram of a console of the system of FIG. 1A, in accordance with some embodiments.

FIG. 1B is a block diagram of various components of a console 125 of the imaging module 120. The console 125 includes one or more processors 130 and memory 140 (e.g., non-transitory computer-readable medium) having stored thereon logic modules that, when executed by the processor 130, are configured to perform operations as described below. The console 125 is communicatively coupled with the display 105 and the ureteroscope 110.

The logic modules include imaging logic 141 and image processing logic 142. The imaging logic 141 is configured to retrieve unprocessed imaging data from the ureteroscope 110 and deliver processed imaging data to the display 105. The imaging logic 141 may communicate with the remote interface 118 so as to render images on the display as defined by the operator 30.

The image processing logic 142 includes image augmenting logic 143, object tracking logic 144, and object sizing logic 145. The image augmenting logic 143 is described below in relation to FIGS. 2A-2C. The object tracking logic 144 is described below in relation to FIGS. 3A-3C and the object sizing logic 145 is described below in relation to FIGS. 4A-4D.

The console 125 may include other hardware or electrical components to facilitate operation of the imaging module 120 and the ureteroscope 110 such as power supplies, I/O ports, power management modules, signal conditioners, processing electronics, GUI signal processing units, computational electronics, graphical processing units, field-programmable gate arrays and the like.

Figure 2B:
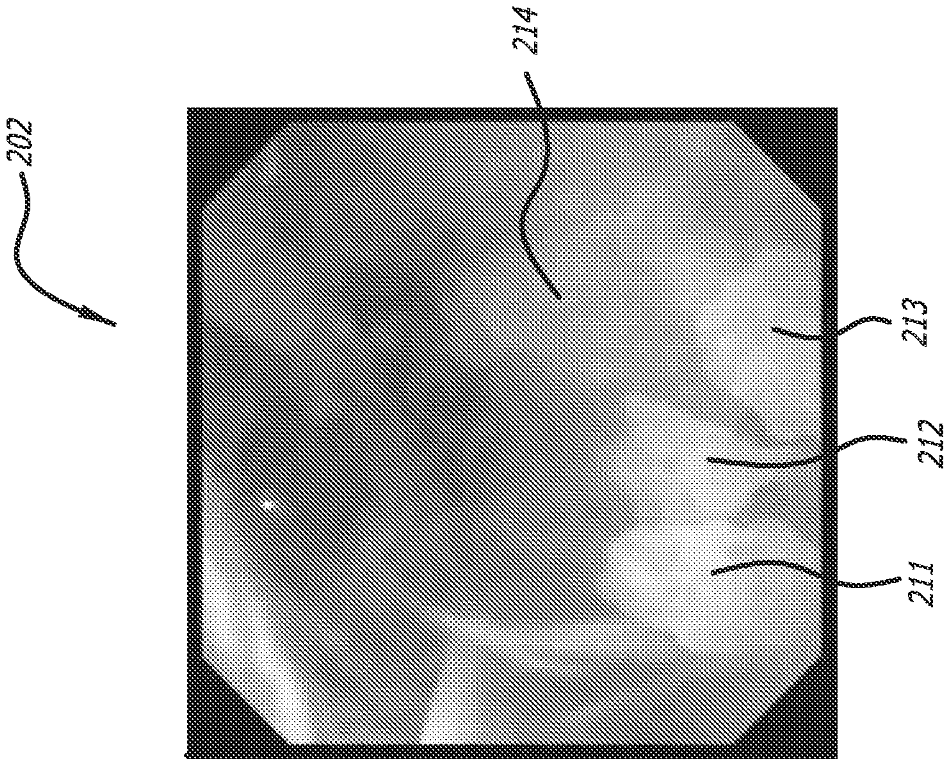
FIG. 2B is an exemplary improved image of the raw ureteroscope image of FIG. 2A, in accordance with some embodiments.
Figure 2A:
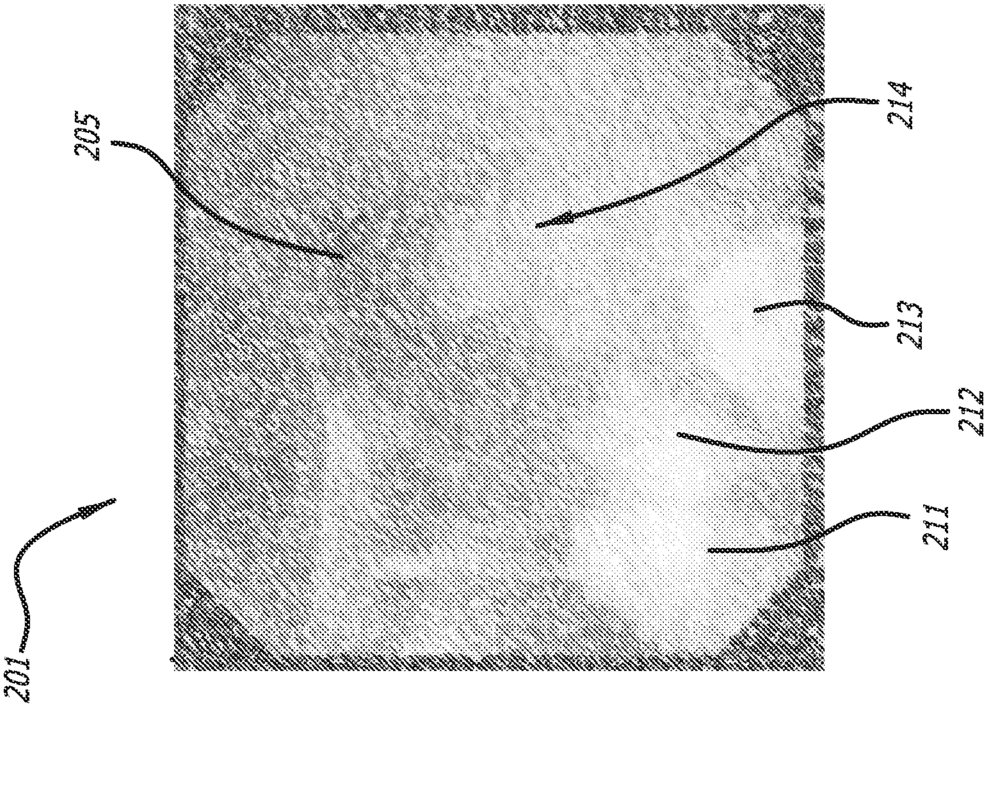
FIG. 2A is an exemplary raw ureteroscope image, in accordance with some embodiments.

FIG. 2A illustrates an exemplary raw ureteroscope image 201 as may be acquired during the ablation of a kidney stone. During ablation of the kidney stone, fragments of different sizes may be broken off and separated from stone. Some fragments may be small enough (e.g., dust) to exit the patient via the urinary tract without further ablation. Other fragments may require further ablation or removal from the patient via a retrieval device. In some instances, the quantity of separated smaller fragments, including dust particles, may be so numerous so as to obstruct visibility of other objects via the ureteroscope 110. The image 201 illustrates how small fragments 205 may obstruct the view of larger fragments 211-214. As such, enhancing visibility of the larger fragments 211-214 may help facilitate further ablation or retrieval of the larger fragments 211-214.

FIG. 2B illustrates an augmented ureteroscope image 202 after image processing via the image augmenting logic 143. As shown, the image augmenting logic 143 has effectively removed the small fragments 205 from the raw image 201 to provide for a clearer visualization of the larger fragments 211-214 in the augmented image 202. The image augmenting logic 143 may include one or more image analysis and processing algorithms (e.g., image subtraction, image comparison, or median filter technics, for example) to differentiate objects that are transient across video image frames from objects that are persistent across video image frames. For example, the smaller fragments 205 may be fluidly suspended within the urinary tract and as such may be transiently displaced by fluid flow across the video image frames. The larger fragments 211-214 may be less fluidly suspended than the smaller fragments 205 and as such may be persistently located across the multiple video image frames. As such, the transient smaller fragments 205 may obstruct the camera's view of portions of the larger fragments 211-214 in some frames while providing an unobstructed view of the portions in other frames. Upon differentiation of the transient fragments 205 from the persistent fragments 211-214, the image augmenting logic 143 may effectively remove the transient fragments 205 from the raw image 201 leaving a clearer view of the persistent fragments 211-214 as illustrated in the augmented image 202. By way of summary, the image augmenting logic 143 may generate the augmented image 202 by removing the transient fragments 205 from the raw image 201.

Figure 2C:
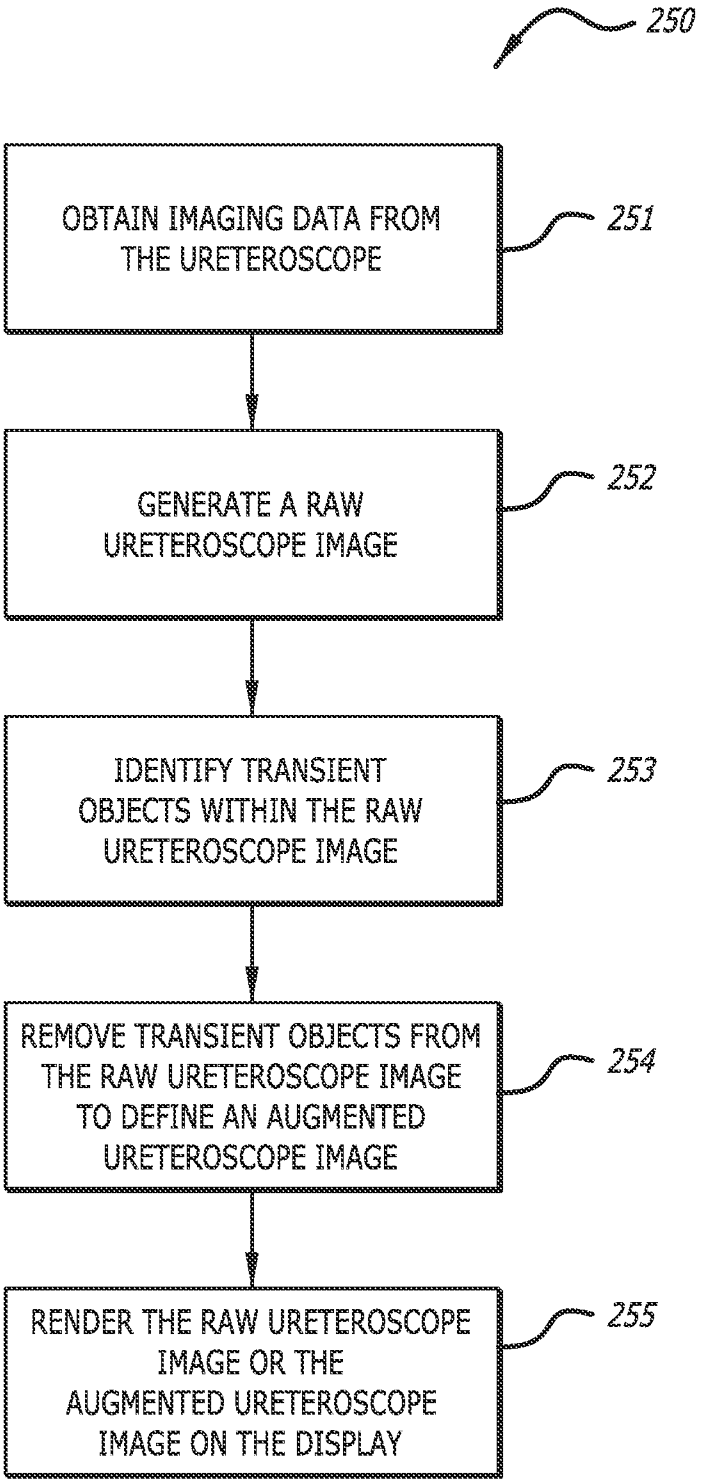
FIG. 2C is an exemplary flow diagram of an imaging process of the ureteroscope system, in accordance with some embodiments.

FIG. 2C is a flow chart 250 illustrating exemplary process steps for defining and displaying the augmented image 202 on the display 105, in accordance with some embodiments. The process includes obtaining imaging data from the ureteroscope (step 251) and generating the raw ureteroscope image 201 from the imaging data (step 252). The process further includes identifying transient objects (e.g., fragments 205) across multiple frames of the raw ureteroscope image 201 (step 253). Once the transient objects are identified, the augmented image 202 is generated by removing or subtracting the transient objects from the raw ureteroscope image 201 (step 254). Thereafter, the raw ureteroscope image 201 or the augmented image 202 is selectively rendered on the display 105 (step 255).

Figure 3B:
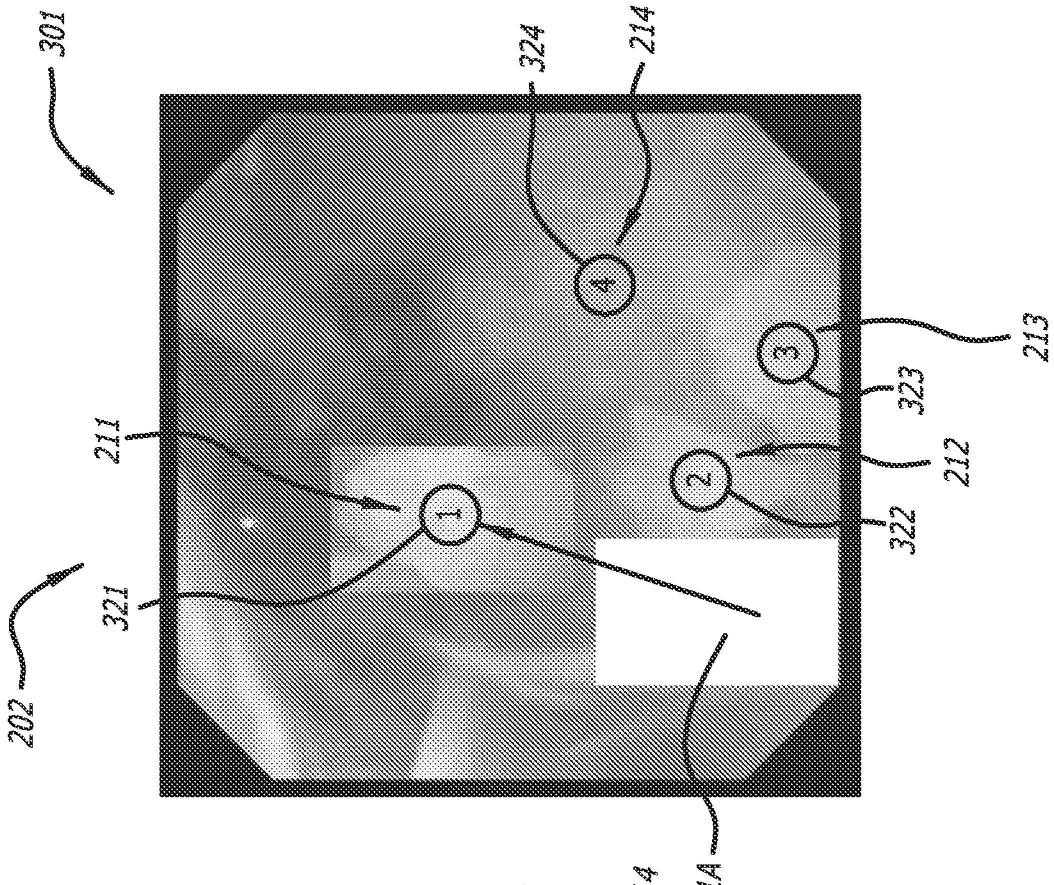
FIG. 3B is the ureteroscope image of FIG. 3A at a subsequent point in time in relation to FIG. 3A, in accordance with some embodiments.
Figure 3A:
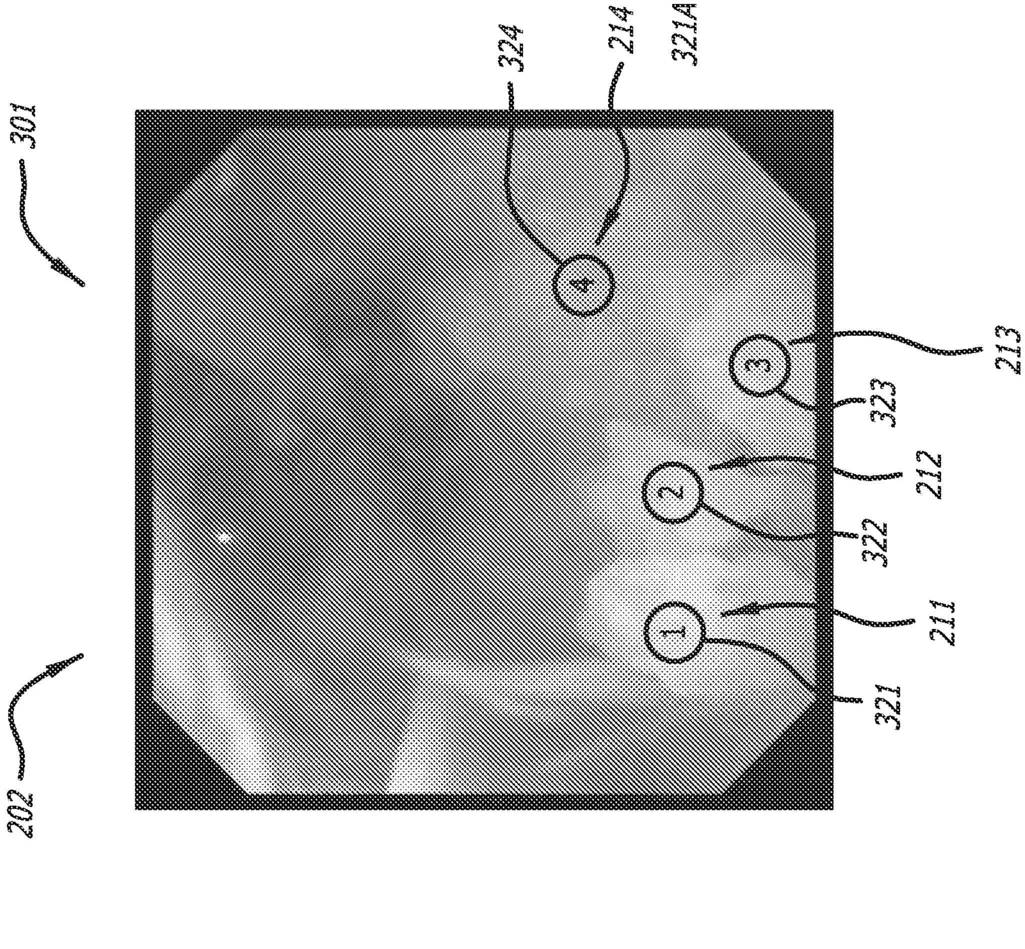
FIG. 3A is an exemplary improved ureteroscope image including a tracking overlay, in accordance with some embodiments.

FIGS. 3A-3B illustrate a tracking overlay 301 displayed on top of the augmented image 202. FIG. 3A illustrates the augmented image 202 including the fragments 211-214 at a first point in time. FIG. 3B illustrates the augmented image 202 including the fragments 211-214 at subsequent point in time. As shown, the fragment 211 has been displaced from a first location in FIG. 3A to a second location in FIG. 3B. During lithotripsy, stone fragments may be displaced due to fluid flow or the laser ablation process. In some instances, it may be difficult for an operator to visually track the position of a stone fragment, such as the fragment 211. In some instances, searching to relocate a fragment may cause a delay in the lithotripsy process. Hence, it may be advantageous for the imaging system 100 to include object tracking logic 144 configured to track the location of defined stone fragments within the augmented image 202. Such tracking may improve the situational awareness and reduce the cognitive load of the operator.

In some embodiments, the object tracking logic 144 may assign identification indicia 321-324 to the stone fragments 211-214, respectively. By assigning identification indicia, the operator may more easily re-identify and track the location of the identified stone fragments 211-214. In some, embodiments, the object tracking logic 144 may automatically assign the identification indicia to defined fragments within the video image. In other embodiments, the object tracking logic 144 may be configured to facilitate manual selection (e.g., via a mouse pointer) of stone fragments to be identified and tracked. In some embodiments, other tracking indicia may also be shown in the tracking overlay 301 such as the arrow 321A showing a displacement path, for example. In the illustrated embodiment, the tracking overlay 301 may be displayed on top of the augmented image 202 or the raw image 201.

Figure 3C:
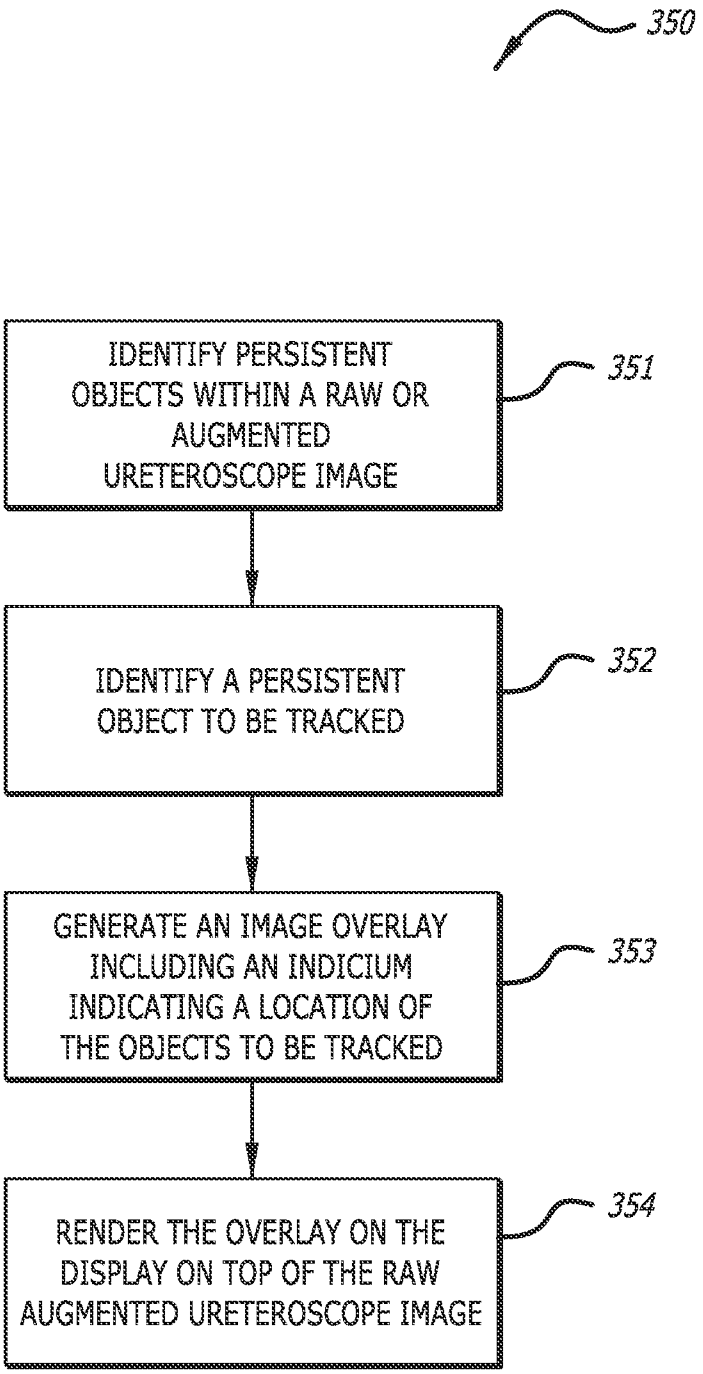
FIG. 3C is an exemplary flow diagram of a tracking process of the ureteroscope system, in accordance with some embodiments.

FIG. 3C a flow chart 350 illustrating exemplary process steps for tracking objects within the raw ureteroscope image 201 or the augmented image 202, in accordance with some embodiments. The process includes identifying persistent objects (e.g., fragments 211-214) across multiple frames of the raw ureteroscope image 201 (step 351). Once the persistent objects (e.g., objects 211-214) are identified, one or more of the persistent objects are identified as objects to the tracked (step 352). An overlay is then generated including indicia (e.g., identification indicia 321-324) indicating the location of the tracked objects (step 353). Thereafter, the overlay 301 is rendered on top of the raw ureteroscope image 201 or the augmented image 202 on the display 105 (step 354).

Figure 4C:
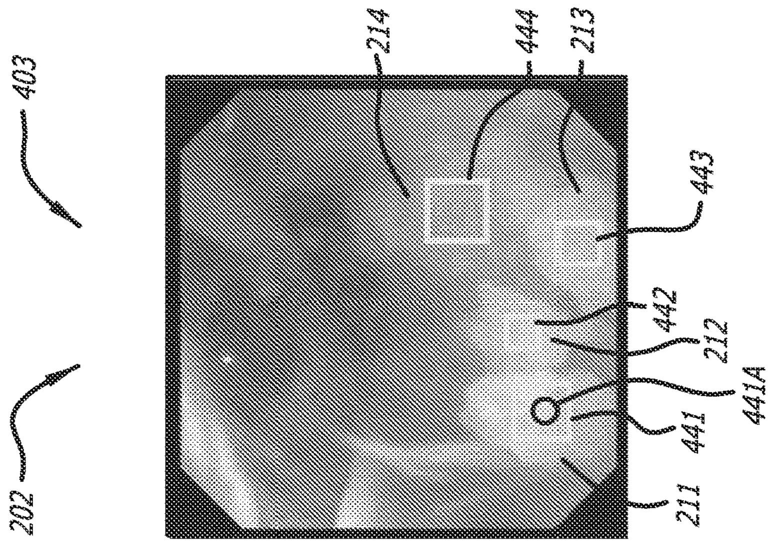
FIG. 4C is an exemplary improved ureteroscope image including an overlay showing size indicia of objects in the image, in accordance with some embodiments.
Figure 4B:
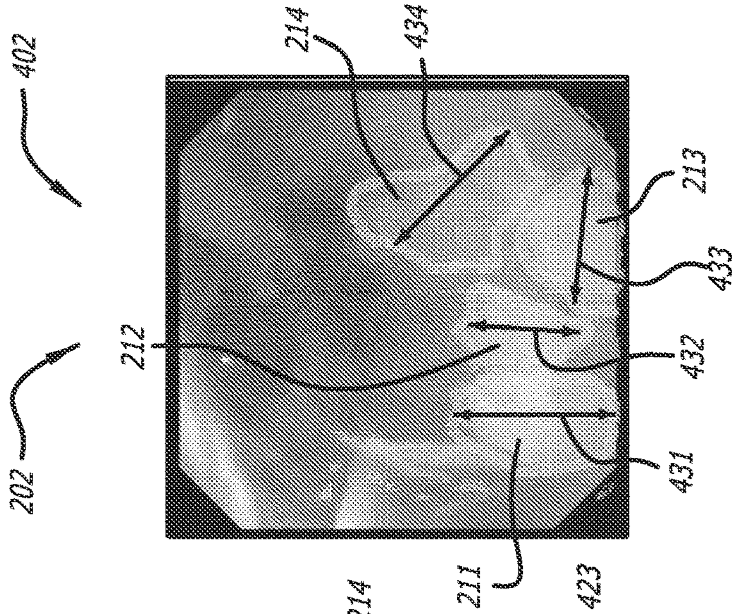
FIG. 4B is an exemplary improved ureteroscope image including an overlay showing maximum length lines of objects in the image, in accordance with some embodiments.
Figure 4A:
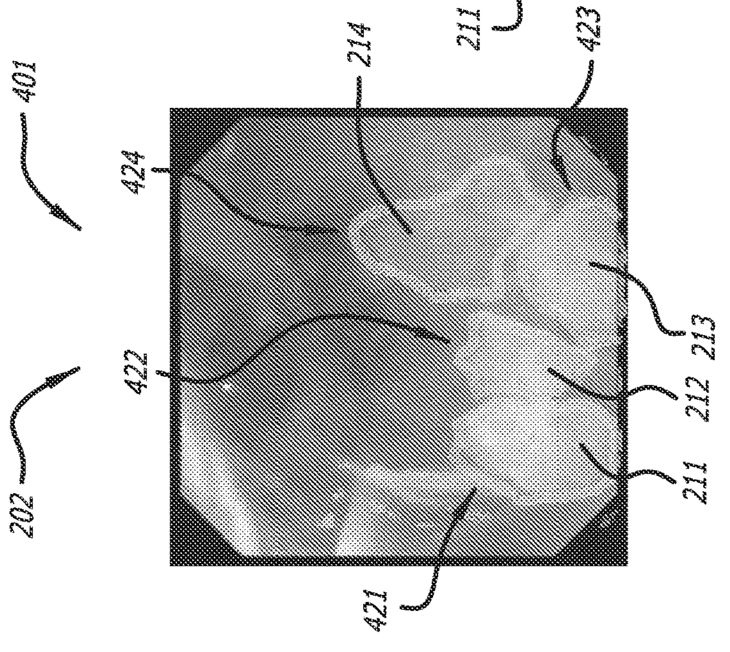
FIG. 4A is an exemplary improved ureteroscope image including an overlay showing highlighted circumferential edges of objects in the image, in accordance with some embodiments.

FIGS. 4A-4C illustrate the augmented image 202 including additional exemplary overlays that, in some embodiments, may be associated with a sizing process implemented via the object sizing logic 144. FIG. 4A illustrates an edge highlighting overlay 401 displayed on top of the augmented image 202. By way of example as shown in FIG. 4A, the object sizing logic 144 has defined and highlighted (or otherwise made more visible) circumferential edges 421-424 extending around each of the fragments 211-214, respectively. By highlighting the circumferential edge of a stone, the operator may more easily visualize the size and shape of the fragment and/or identify a portion of the stone at which to aim the laser for ablation. In some embodiments, the object sizing logic 144 may include image process algorithms (e.g., algorithms know as Canny, Sobel, and Gaussian) to identify the circumferential edge. In some embodiments, the object sizing logic 144 may automatically define fragments within the image for edge highlighting. For example, the object sizing logic 144 may perform a size assessment of persistent fragments within the image and highlight the circumferential edge of fragments exceeding a defined size stored in memory 140. In some embodiments, the object sizing logic 144 may be configured to facilitate manual selection (e.g., via a mouse pointer) of stone fragments to include edge highlighting. In the illustrated embodiment, the edge highlighting overlay 401 may be displayed on top of the augmented image 202 or the raw image 201.

FIG. 4B illustrates a fragment length overlay 402 displayed on top of the augmented image 202 together with the edge highlighting overlay 401 of FIG. 4A. In some embodiments, the fragment length overlay 402 may be singularly displayed over the augmented image 202. The object sizing logic 144 may define size indicating lengths of defined fragments, such as the lengths 431-434 of the fragments 411-414, respectively as illustrated. Each of the lengths 431-434 may be a defining characteristic of the respective stone size (e.g., an imaged area). In some embodiments, the size indicating length may be a maximum distance between two points along the circumferential edge. In some embodiments, the lengths 431-434 may be shown as line indicia in the overlay 402 which may help the operator determine if further ablation or fragmentation is warranted. In some embodiments, the object sizing logic 144 may define measurements of the size indicating lengths 431-434 and display length measurement value indicia in the overlay 402. In some instances, the size indicating length may facilitate a decision by the operator that further ablation of a fragment is needed or that the patient can pass fragment through the urinary tract naturally. In similar fashion to edge highlighting, the object sizing logic 144 may automatically define fragments for length indication according to defined criteria and/or facilitate manual selection of fragments for length indication.

FIG. 4C illustrates a fragment size overlay 403 displayed on top of the augmented image 202. The object sizing logic 144 may define a size or image area of a fragment bay calculating the area enclosed by the circumferential edge. Size indicating indicia of defined fragments, such as the size indicating indicia 441-444 of the fragments 211-214, respectively may provide a size representation of fragments allowing the operator to ascertain sizes of the fragments 211-214, for example, with respect to each other. In the illustrated embodiment, the indicia 441-444 include a square shape. In other embodiments, indicia 441-444 may be any other polygon, chevron, an outline of the fragment or any other type of a marking suitable for visually representing a size of the fragment. In similar fashion to the length indication, the object sizing logic 144 may automatically identify fragments for size indication according to defined criteria and/or facilitate manual selection of fragments for size indication.

In some embodiments, the object sizing logic 144 may include size criteria associated with the urinary tract such as a flow path area of a ureter, for example. The object sizing logic 144 may further determine if a fragment size exceeds a defined size criterion, and if so, the object sizing logic 144 may include a secondary indicum such as the indicium 441A, change the shape of the size indicium, change a color of the size indicium, or provide visual indication in any suitable differentiating fashion. By way of summary, the object sizing logic 144 may automatically indicate to the operator which fragments need further fragmentation and which fragments may naturally pass through the urinary tract out of the patient.

Figure 4D:
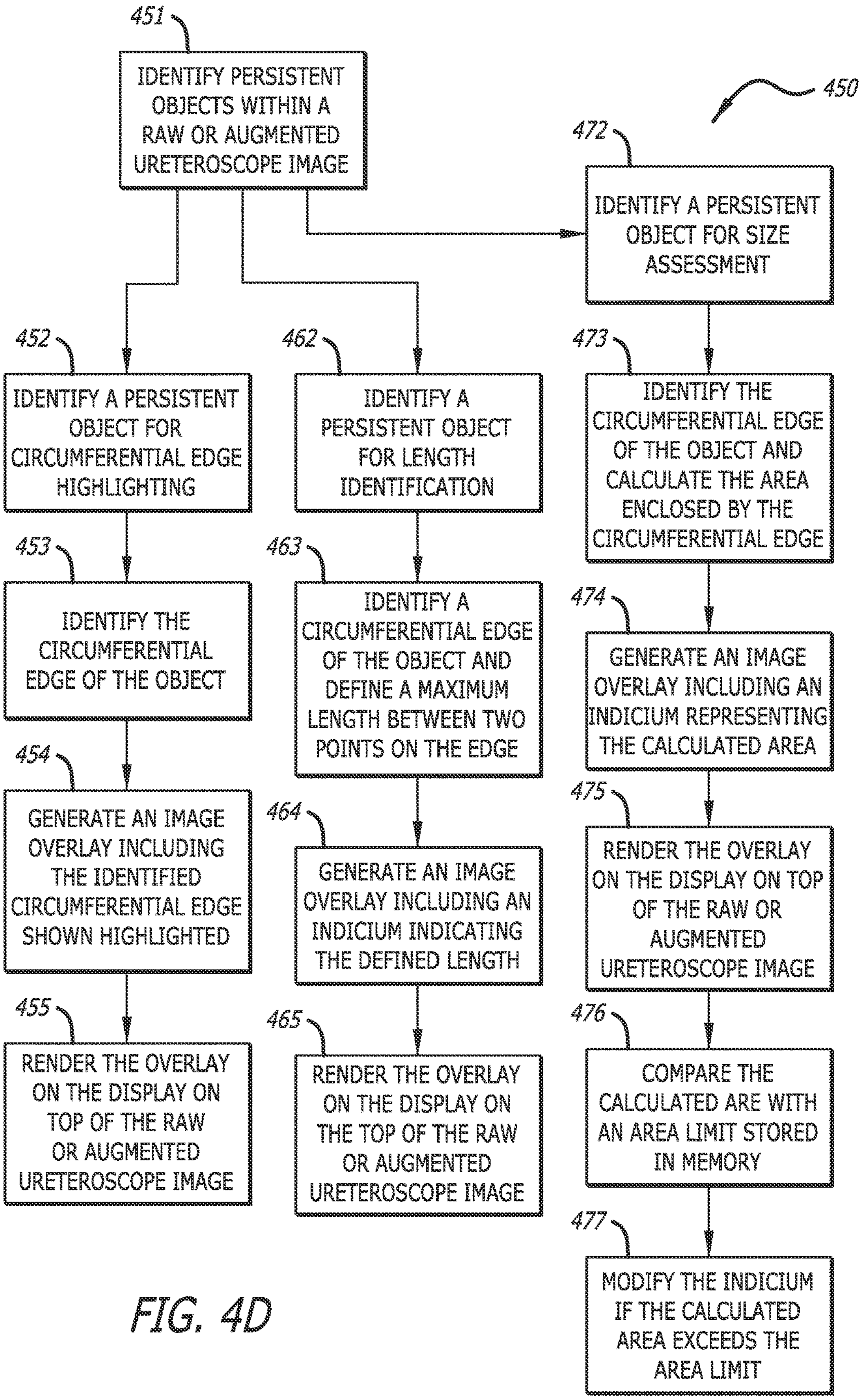
FIG. 4D is an exemplary process flow diagram of an edge highlighting process, a maximum length line determination process, and a size determination process of the ureteroscope system, in accordance with some embodiments.

FIG. 4D is a flow chart 450 illustrating exemplary process steps for assessing/estimating the size of objects within the raw ureteroscope image 201 or the augmented image 202, in accordance with some embodiments. The process includes identifying persistent objects (e.g., fragments 211-214) across multiple frames of the raw ureteroscope image 201 (step 451). Once the persistent objects are identified, one or more the persistent objects are identified as objects for circumferential edge highlighting (step 452). The circumferential edges (e.g., edges 421-424) are identified (step 453). An overlay is then generated including highlighting of the identified circumferential edges (step 454). Thereafter, the overlay 401 is rendered on top of the raw ureteroscope image 201 or the augmented image 202 on the display 105 (step 455). With the circumferential edge highlighted, the operator may more easily visually assess the size of the objects.

With further reference to FIG. 4D, the process steps for assessing/estimating the size of objects may further include identifying one or more the persistent objects for which determining a characteristic length may be advantageous (step 462). The process further includes, for each of the identified objects, identifying a circumferential edge and determining a line defining a maximum length between two points on the circumferential edge (step 463). The overlay 402 is then generated including the lines extending across the identified objects (step 464). Thereafter, the overlay is rendered on top of the raw ureteroscope image 201 or the augmented image 202 on the display 105 (step 465).

Again, with reference to FIG. 4D, the process steps for assessing/estimating the size of objects may further include identifying one or more the persistent objects for size assessment/estimation (step 472). The process further includes, for each of the identified objects, identifying a circumferential edge and calculating an area enclosed by the circumferential edge (step 473). The overlay 403 is then generated including indicia representing the calculated area (step 474). Thereafter, the overlay is rendered on top of the raw ureteroscope image 201 or the augmented image 202 on the display 105 (step 475). In some embodiments, the process steps may include comparing the calculated area with an area size limit stored in memory (step 476). The process may further include modifying the size indicium if the calculated area exceeds the size limit (step 477).

Figure 5:
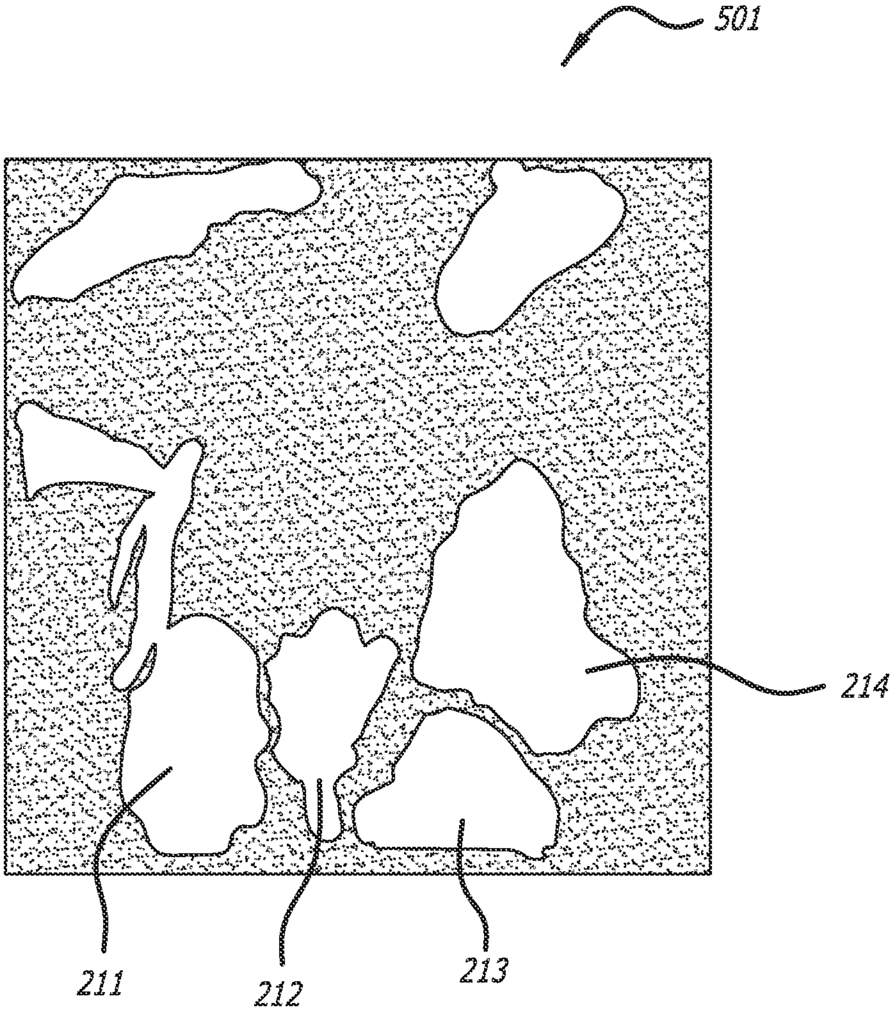
FIG. 5 is an illustration of an exemplary high-contrast black-and-white view of the improved image of FIG. 2B, in accordance with some embodiments.

FIG. 5 illustrates a high-contrast ureteroscope image 501 after further image processing of the augmented image 202 via the image augmenting logic 143. The high-contrast image 501 is a high-contrast black/white image showing the fragments 211-214. The high black/white contrast enables the operator to more easily visualize and focus on the objects of importance within the image such as the fragments 211-214. Any or all overlays described above may be disposed on top of the high-contrast image 501.

The image processing logic 142 may facilitate rendering of any combination of the images 201, 202, and 501 with the overlays 301, 401, 402, and 403. The image processing logic 142 may also facilitate switching between any of the combinations at will by the operator via the GUI 151 or the remote interface 118.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A ureteroscope system comprising:
- a ureteroscope configured for insertion into a urinary tract of a patient body, the ureteroscope comprising:
  - an elongate flexible shaft, and
  - a camera disposed at a distal end of the elongate flexible shaft; and
- an image processing module operatively coupled with the ureteroscope, the image processing module comprising a console including one or more processors and a non-transitory computer-readable medium having stored thereon logic that, when executed by the one or more processors, is configured to perform operations, comprising:
  - receiving imaging data including a first image, wherein:
    - the first image includes a plurality of objects including a first subset of the plurality of objects that obstructs visibility of one or more objects of a second subset of the plurality of objects, and
    - the first subset of the plurality of objects and the one or more objects of the second subset include fragments of a kidney stone;
  - generating a second image including the second subset of the plurality of objects in a visibly unobstructed view;
  - causing rendering of the first image or the second image on a display;
  - identifying circumferential edges of the one or more objects within the first image or the second image;
  - defining a size of the one or more objects within the first image or the second image, the size defined by calculating an area enclosed by the circumferential edge;
  - defining a sizing image overlay, wherein the sizing image overlay includes size indicia associated with the size of the one or more objects and each size indicium provides a visual indication of a respective size of each object;
  - comparing each calculated area with an area limit stored in the non-transitory computer-readable medium; and
  - modifying the size indicium if a respective calculated area exceeds the area limit.

2. The system of claim 1, wherein the operations further comprise causing the rendering of the second image on the display.

3. The system of claim 1, wherein:
- the imaging data comprises video imaging data, and
- the first image and the second image comprise video images.

4. The system of claim 1, wherein the operations further comprise removing the first subset from the first image to define the second image.

5. The system of claim 1, wherein:
the second subset includes objects that are persistent within the first image, and
the first subset includes objects that are transient within the first image.

6. The system of claim 1, wherein the operations further comprise tracking locations of the one or more objects within the first image or the second image.

7. The system of claim 6, wherein the operations further comprise defining a tracking image overlay, the tracking image overlay including tracking indicia associated with the tracked one or more objects.

8. The system of claim 7, wherein the operations further comprise causing rendering of the tracking image overlay on top of the first image or the second image on the display.

9. The system of claim 1, wherein:
the operations further comprise defining an edge-highlighting image overlay, and
the circumferential edges are highlighted in the edge-highlighting image overlay.

10. The system of claim 9, wherein the operations further comprise causing rendering of the edge-highlighting image overlay on top of the first image or the second image on the display.

11. The system of claim 1, wherein the operations further comprise causing rendering of the sizing image overlay on top of the first image or the second image on the display.

12. The system of claim 1, wherein the operations further comprise defining maximum lengths of the one or more objects within the first image or the second image, each maximum length defined by a maximum distance between two points of the circumferential edge of each respective object.

13. The system of claim 12, wherein the operations further comprise defining a length image overlay, the length image overlay including a line indicium visually representing each respective maximum length.

14. The system of claim 13, wherein the operations further comprise causing rendering of the length image overlay on top of the first image or the second image on the display.

* * * * *